(12) United States Patent
Nazaroff et al.

(10) Patent No.: US 9,356,465 B2
(45) Date of Patent: May 31, 2016

(54) RINSING GLASS AND CHARGER COMBINATION FOR A POWER TOOTHBRUSH

(75) Inventors: Peter George Nazaroff, Seattle, WA (US); Peter Lewis Shreve, Issaquah, WA (US); Ahren Karl Johnson, North Bend, WA (US); Chi Hung Li, Hong Kong (HK); Wai Hang Raymond Lo, Hong Kong (HK)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 92 days.

(21) Appl. No.: 13/989,828

(22) PCT Filed: Dec. 19, 2011

(86) PCT No.: PCT/IB2011/055780
§ 371 (c)(1),
(2), (4) Date: May 28, 2013

(87) PCT Pub. No.: WO2012/085819
PCT Pub. Date: Jun. 28, 2012

(65) Prior Publication Data
US 2013/0257369 A1 Oct. 3, 2013

Related U.S. Application Data
(60) Provisional application No. 61/426,071, filed on Dec. 22, 2010.

(51) Int. Cl.
*H02J 7/00* (2006.01)
*H02J 7/02* (2016.01)
*A61C 17/22* (2006.01)
(52) U.S. Cl.
CPC ............... *H02J 7/025* (2013.01); *A61C 17/224* (2013.01)

(58) Field of Classification Search
CPC ................................ Y02E 60/12; H02J 7/025
USPC .................................................. 320/107, 108
See application file for complete search history.

(56) References Cited

U.S. PATENT DOCUMENTS

2005/0007065 A1* 1/2005 Freas et al. .................... 320/107
2011/0163714 A1 7/2011 Ettes et al.

FOREIGN PATENT DOCUMENTS

DE 29618742 U1 1/1997
DE 10218124 A1 11/2003
(Continued)

OTHER PUBLICATIONS

AAK'S AA Induction Battery: Recharges in a Cup?, http://www.engadget.com/2006/10/20/aaks-aa-induction-battery-rechares-in-a-cup/, Apr. 27, 2010.

*Primary Examiner* — Edward Tso
*Assistant Examiner* — Ahmed Omar

(57) ABSTRACT

The combination of a power toothbrush and a charging system includes a charging base unit (12) having a charging coil (22) wound around the interior surface (20) of a portion of the charging base unit, and connectable to a source of electric power and a rinsing vessel (26) adapted to hold a toothbrush, the rinsing glass having a lower surface (27) configured to fit onto the upper surface (14) of the charging unit. The vessel is configured to hold a toothbrush in such a manner to prevent the toothbrush from tipping over when placed in the vessel, and further configured relative to the base unit that charging of the power toothbrush can occur between a pickup coil (46) in the handle of the toothbrush and the charging coil in the base charging unit.

12 Claims, 2 Drawing Sheets

(56) References Cited

FOREIGN PATENT DOCUMENTS

| | | | |
|---|---|---|---|
| DE | 102007053985 A1 | 5/2009 | |
| FR | 2683713 A1 | 5/1993 | |
| JP | 2001286407 | * 10/2001 | ............ A47B 67/02 |
| JP | 2001286407 A | 10/2001 | |
| WO | 2010026528 A2 | 3/2010 | |

* cited by examiner

RINSING GLASS AND CHARGER COMBINATION FOR A POWER TOOTHBRUSH

This invention relates generally to charging systems for power toothbrushes, and more specifically concerns a charging system which also incorporates a rinsing glass for the user.

Power toothbrushes often are used with a charger unit using inductive-type charging to charge the battery in the power toothbrush. For inductive charging, the coil on a charger unit that is connected to a wall outlet is inductively coupled to a pickup coil inside the base of the power toothbrush. The resulting flux between the two coils, with the battery in the toothbrush being connected to the pickup coil in the base of the toothbrush, results in the battery being charged. The charger is arranged to hold and charge the toothbrush when the toothbrush is not in use.

With such a charging arrangement, a user will typically rinse their brushed teeth using a separate glass following use of the toothbrush. Many users, however, find the use of a separate glass for rinsing inconvenient. Manual toothbrush users, on the other hand, have no need for a separate charging unit, but do need to rinse following toothbrush use, just as users of power toothbrushes do. Often, the manual toothbrush user will use the same glass for both holding the toothbrush when not in use and for rinsing.

Accordingly, it would be desirable to combine the holding and charging function for a power toothbrush with a rinsing function, in a single unit. However, there are challenges to provide an efficient charging system with such an arrangement, given the much greater distance between the respective coils in the charger and the handle than is the case for a conventional charger arrangement.

Accordingly, what is disclosed herein is a combination of a power toothbrush and a charging system therefor, comprising: a base unit having a concave upper surface portion with a charging coil wound around an interior surface thereof, the base unit being connectable to a source of electrical power, the base unit further having an outer lip at the upper edge thereof; a rinsing vessel having a lower surface configured to fit onto the concave upper surface portion of the base unit and the outer lip of the upper edge of the base unit, the rinsing vessel shaped and adapted to hold a toothbrush therein at an angle in the range of 0°-45° from vertical, the vessel having sides configured to prevent the toothbrush from tipping over when placed in the vessel, and further configured relative to the base unit and a handle portion of the toothbrush that charging of a power toothbrush can occur over a distance in the range of 15-35 mm between a pickup coil in the handle of the toothbrush and the charging coil in the base unit.

Figure 1:
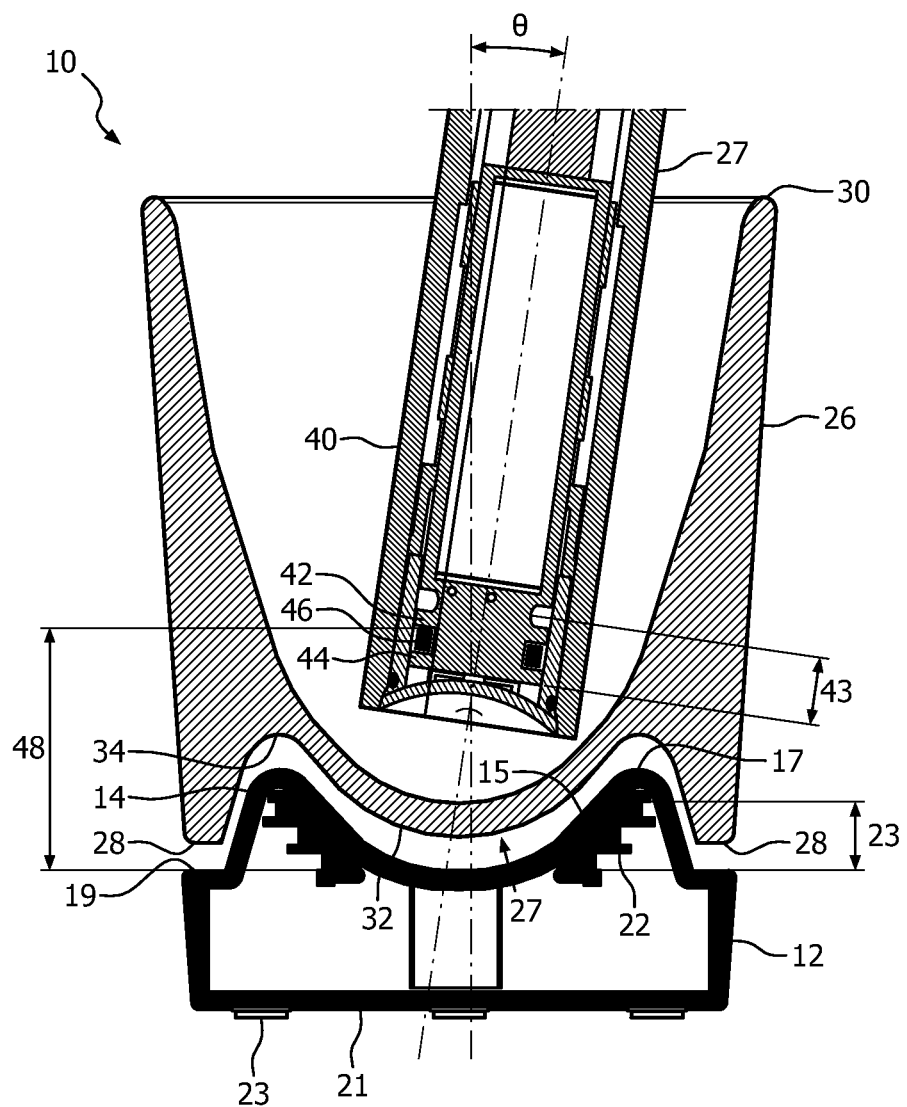
FIG. 1 is a cross-sectional view of the combination of a charging unit, an associated rinsing glass and a portion of a toothbrush handle positioned at a desired orientation relative to the rinsing glass.

A combination charging system and rinsing glass suitable for charging a power toothbrush is shown generally at 10. It includes a charger portion base unit 12 which in the embodiment shown is approximately 30 mm high. The charger portion can have various cross-sectional configurations, including round, square, oval, etc. An upper surface 14 of the charger 12 has a concave center portion 15 with an outer edge or lip 17. The upper surface extends downwardly from lip 17 to a flat surrounding outer part 19, which is approximately 5 mm wide. From outer part 19, charger 12 extends downwardly to a flat base element 21. Charger 12 is made from ABS material, approximately 2 mm thick. Wound around the interior surface 20 of the concave center portion 15 is a charging coil 22. In the embodiment shown, charging coil 22 has approximately 41±10 windings. The height 23 of the charging coil is an important dimension in the charging system, approximately 9 mm in the embodiment shown, although this can be varied to some extent, within a range of 5-25 mm.

Figure 2:
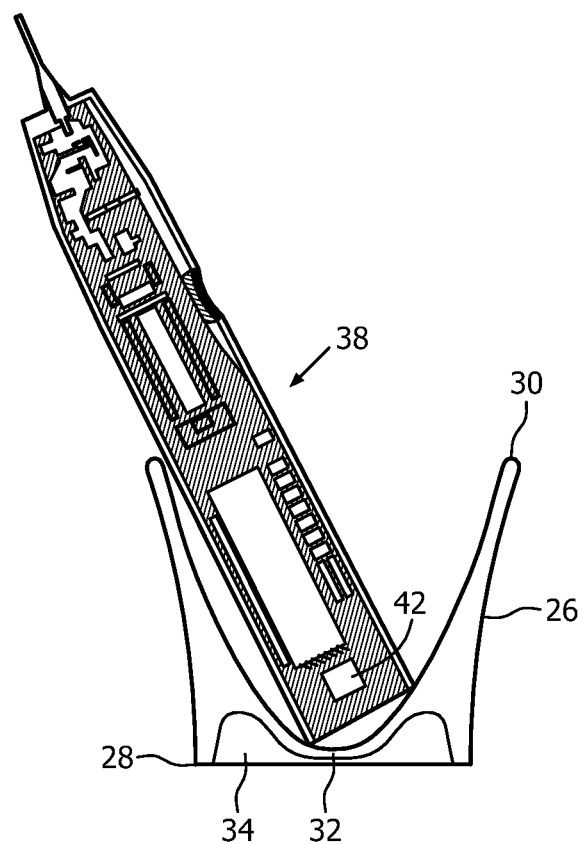
FIG. 2 is a cross-sectional view showing a suitable position of the toothbrush handle in a glass which fits onto the charger of FIG. 1.
Figure 3:
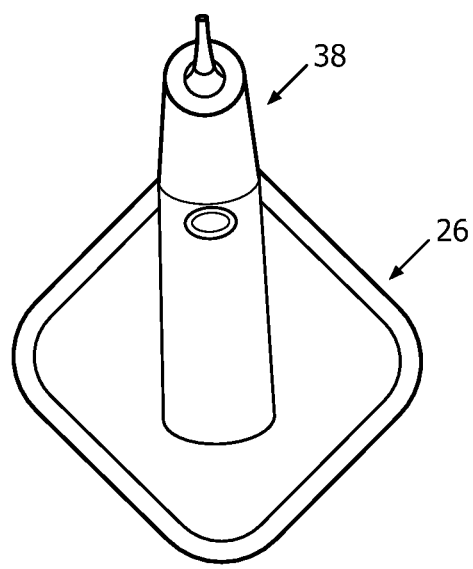
FIG. 3 is a top plan view of the charging system glass with a power toothbrush positioned therein.

A second portion of the charging system 10 is a vessel 26. Vessel 26 may be made of glass or plastic, although glass is generally preferred. Vessel 26 functions in the present arrangement both as a holder for a power toothbrush 27 when it is not in use and as a rinsing glass for the user when brushing is complete. Vessel 26 is approximately 80 mm high and slightly tapers outwardly from a lower boundary edge 28 to an upper edge 30 thereof. In the embodiment shown, vessel 26 is approximately square in cross-section with rounded corners, as shown in FIG. 3, although other configurations, including circular, can be used. The configuration of the lower edge is such that it mates with the upper surface 14 of charger 12, in particular, the flat outer part 19 thereof. The base or lower surface 27 of vessel 26 has a center portion 32 which is convex, as shown in FIGS. 1 and 2, surrounded by a trough portion 34 which is positioned between the convex portion 32 and the lower boundary edge 28 of the vessel. In the embodiment shown, the convex portion 32 has a thickness of approximately 3 mm, thin enough to permit charging, but thick enough to maintain structural integrity and strength, although this can be varied to some extent. The lower boundary edge 28 in the embodiment shown is approximately 80 mm in diameter or there is 80 mm between opposing edges, if the edge 28 has a square configuration. Trough portion 34 is configured and arranged to fit over outer edge/lip 17 of the charger so that the glass rests securely on the charger when not in use and reliably supports the power toothbrush when it is positioned in the glass.

A third part of the charging system is the power toothbrush 38 itself. When not in use, the toothbrush is positioned within the glass, as shown in the figures. Typically, the vessel 26 is configured so that the handle of the toothbrush sits at an angle θ of 28° in the embodiment shown. This angle can vary, such as over a range of 0-45°. However, the arrangement must be such that the toothbrush can sit in the glass without tipping the glass over. Typically, for a toothbrush which is 192 mm long, 83 mm thereof will be within the vessel 26, i.e. below the upper edge 30 of the vessel.

The toothbrush generally can be any power toothbrush. However, for best results, a lower end of handle 40 portion of the toothbrush (FIG. 1) includes a ferrite core 42, which improves the flux coupling. In the embodiment shown, ferrite core 42 fits in the center of the lower end of the handle and has an exterior diameter of approximately 9.4 mm and a height 43 of approximately 8.0 mm. The edges of the core are typically chamfered. The ferrite core assists in the charging function for the combination. Wound around the lower end of the handle in a bobbin portion 44 thereof is a pickup coil 46. In the embodiment shown, the bobbin portion 44 has a base diameter of approximately 12.4 mm and an outer edge diameter of approximately 17.5 mm. The open space for the winding is approximately 3.9 mm wide. The pickup coil 46 in the embodiment shown has approximately 60 windings.

The distance 48 between the bottom of the charging coil and the top of the pickup coil, generally referred to as the charging distance, is another significant dimension and, in the embodiment shown, is 24 mm, within a range of 15-35 mm. This is in contrast to a typical charging distance of 1 mm or so. The charging system also typically includes a capacitor, so that the two coils can be tuned to improve charging efficiency. In the embodiment shown, there is maximum coupling at 80 KHz.

The above arrangement provides both a reliable charging system for the power toothbrush, but also provides a convenient rinsing glass for the user with the same combination of elements. The toothbrush is positioned in the rinsing glass when the toothbrush is not in use, as opposed to being positioned within a conventional charging unit.

In operation, the user will first remove the toothbrush from the glass vessel 26, with the toothbrush being fully charged. The user will then brush his/her teeth in a conventional manner, rinse the toothbrush and then remove the glass from the charger and use the glass to rinse out the mouth. The glass will then be rinsed with clean water and repositioned on the charger, at which point the toothbrush can be positioned in the glass for storage and recharging until the next use.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. The combination of a power toothbrush and a charging system therefor, comprising:
   a base unit comprising:
      an outer lip of an upper edge of the base unit;
      a concave upper surface portion internal to the outer lip;
      a charging coil wound around an interior surface of said concave upper surface, the base unit being connectable to a source of electrical power; and
   a rinsing vessel, removably positioned on the base station, configured to hold a liquid, said rising vessel, comprising:
   a lower surface comprising:
      a convex outer lower surface configured to fit onto an exterior surface of the concave upper surface portion of the base unit and the outer lip of the outer edge of the base unit, wherein the convex outer lower surface extends into the wound charging coil,
      an inner lower surface, matching the outer lower surface, adapted to hold a toothbrush therein, wherein the toothbrush is tipped at an angle in the range of up to 45° from a vertical position, and
   sides extending from the lower surface, the sides being configured to retain the toothbrush at the tipped angle when the toothbrush is placed in the vessel, and further configured relative to the base unit and a handle portion of the toothbrush that charging of a power toothbrush can occur between a pickup coil in the handle of the toothbrush and the charging coil in the base unit.

2. The combination of claim 1, wherein the lower surface configuration substantially matches the configuration and dimensions of the upper surface of the base unit.

3. The combination of claim 1, wherein the rinsing vessel is made of glass.

4. The combination of claim 1, wherein the rinsing vessel is made from a plastic material.

5. The combination of claim 1, wherein the rinsing vessel has an interior configuration such that the toothbrush sits at an angle of approximately 28° from vertical when it is positioned in the concave inner lower surface of the vessel.

6. The combination of claim 1, wherein the toothbrush has a ferrite core positioned in its lower end, and wherein the pickup coil is wound around a bobbin member which surrounds the ferrite core.

7. The combination of claim 1, wherein a charging distance between the charging coil and the pickup coil is approximately 24 mm.

8. The combination of claim 1, wherein the vessel has a thickness of approximately 3 mm at a lower end thereof, adjacent the concave surface of the charger.

9. The combination of claim 1, wherein the height of the charging coil is approximately 9 mm.

10. The combination of claim 1, wherein the pickup coil has approximately 60 windings and wherein the charging coil has approximately 41±10 windings.

11. The combination of claim 1, wherein the charger has a base section which extends downwardly from the outer lip to a lower base element surface which rests on a counter surface in use.

12. The combination of claim 1, wherein a charging distance between the charging coil and the pickup coil is in the range of 15-35 mm.

* * * * *